United States Patent [19]

Turner et al.

[11] Patent Number: 4,656,258
[45] Date of Patent: Apr. 7, 1987

[54] MACROCIN DERIVATIVES

[75] Inventors: Jan R. Turner, Carmel; Veronica M. Krupinski, Greenwood; David S. Fukuda, Brownsburg; Richard H. Baltz, Indianapolis, all of Ind.

[73] Assignee: Eli Lilly and Company, Indianapolis, Ind.

[21] Appl. No.: 743,243

[22] Filed: Jun. 11, 1985

Related U.S. Application Data

[62] Division of Ser. No. 471,628, Mar. 3, 1983, Pat. No. 4,559,301.

[51] Int. Cl.$^4$ ............................................. C07H 17/08
[52] U.S. Cl. ..................................................... 536/7.1
[58] Field of Search ........................................ 536/7.1

[56] References Cited

U.S. PATENT DOCUMENTS

| | | | |
|---|---|---|---|
| 3,326,759 | 6/1967 | Hamill et al. | 167/65 |
| 4,092,473 | 5/1978 | Okamoto et al. | 536/17 |
| 4,205,163 | 5/1980 | Mori et al. | 536/17 |
| 4,268,665 | 5/1981 | Sakakibara et al. | 536/17 R |
| 4,357,325 | 11/1982 | Ose et al. | 424/180 |
| 4,452,784 | 6/1984 | Kirst et al. | 536/7.1 |
| 4,486,584 | 12/1984 | Baltz et al. | 536/7.1 |

OTHER PUBLICATIONS

Kirst, et al., "Jour. of Antibiotics", vol. 35, No. 12, pp. 1675–1682, 1982.
Omura, "Macrolide Antibiotics", Academic Press, Inc. New York, N.Y., pp. V–IX (Contents) and 98–121, 1984.
Derwent Abstract No. 66634C/38 of Japanese Unexamined Patent J5 5043-013, 3-26-80 (Sanraku Ocean).
Derwent Abstract No. 17437C/10 of Japanese Unexamined Patent J5 5011-558, 1-26-80 (Toyo Jozo).
Derwent Abstract No. 79659C/45 of Japanese Unexamined Patent J5 5122-798, 9-20-80 (Toyo Jozo).
Derwent Abstract No. 74422C/42 of Japanese Unexamined Patent J5 5115-899, 9-6-80 (Toyo Jozo).
Okamoto et al., "The Activity of 4''-Acylated Tylosin Derivatives Against Macrolide-Resistant Gram-Positive Bacteria", J. Antibiotics 32, 542–544 (1979).
Okamoto et al., "Physico-Chemical Properties of New Acyl Derivatives of Tylosin Produced by Microbial Transformation", J. Antibiotics 33, 1300–1308 (1980).
Okamoto et al., "Biological Properties of New Acyl Derivatives of Tylosin", J. Antibiotics 33, 1309–1315 (1980).
Okamoto et al., "Studies on the Effects of 3-Acetyl-4'-'-Isovaleryltylosin Against Multiple-Drug Resistant Strains of Staphylococcus aureus", J. Antibiotics 34, 305–312 (1981).
Tsuchiya et al., "Studies of Tylosin Derivatives Effective Against Macrolide-Resistant Strains: Synthesis and Structure Activity Relationships, J. Antibiotics 35, 661–672 (1982).
Derwent Abstract No. 27592A/15 of Japanese Unexamined Patent J5 3021-182, 2-27-78 (Sanraku Ocean).
R. H. Baltz et al., "Genetics and Biochemistry of Tylosin Production by Streptomyces fradiae," Microbiology 1981, pp. 371–375.
R. H. Baltz, et al., "Biosynthesis of the Macrolide Antibiotic Tylosin a Preferred Pathway from Tylactone to Tylosin," The Journal of Antibiotics, vol. 36, No. 2, pp. 131–141, Feb. 1983.

Primary Examiner—Johnnie R. Brown
Attorney, Agent, or Firm—Nancy J. Harrison

[57] ABSTRACT

New macrocin and lactenocin ester derivatives of the formula:

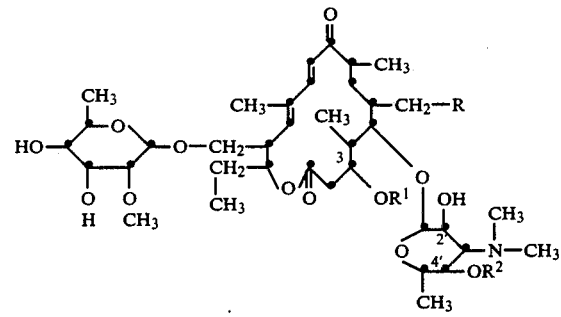

wherein R is formyl or hydroxymethyl; $R^1$ is hydrogen, acetyl or propionyl; $R^2$ is hydrogen or

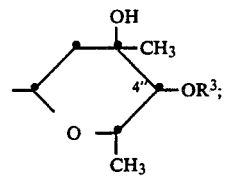

and $R^3$ is hydrogen, acetyl, propionyl, n-butyryl or isovaleryl; provided that one of $R^1$ or $R^3$ must be other than hydrogen; and the acid addition salts thereof; prepared by bioconversion of macrocin or lactenocin with an acylating enzyme system produced by Streptomyces thermotolerans strains, have improved activity against Mycoplasma species.

12 Claims, No Drawings

MACROCIN DERIVATIVES

This application is a division of application Ser. No. 471,628, filed Mar. 3, 1983, now U.S. Pat. No. 4,559,301.

SUMMARY OF THE INVENTION

The present invention relates to new macrocin and lactenocin derivatives having formula 1:

The new macrocin and lactenocin derivatives inhibit the growth of various pathogenic microorganisms. Certain of the derivatives are active against microorganisms which are resistant to tylosin. Several of the derivatives are useful intermediates to other active compounds. Some of the macrocin esters are better absorbed orally than tylosin is and give higher blood levels after oral administration than tylosin does.

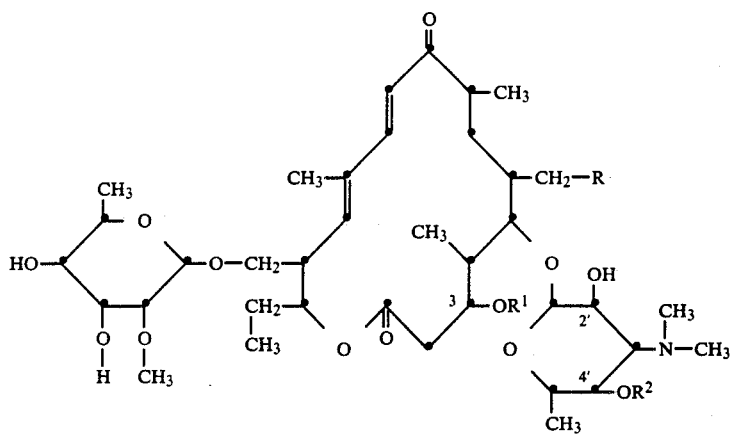

wherein R is formyl or hydroxymethyl; $R^1$ is hydrogen, acetyl or propionyl; $R^2$ is hydrogen or

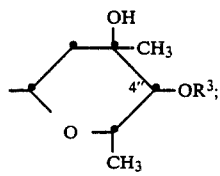

and $R^3$ is hydrogen, acetyl, propionyl, n-butyryl or isovaleryl; provided that one of $R^1$ or $R^3$ must be other than hydrogen; and the acid addition salts thereof; and to methods of preparing these compounds by bioconversion of macrocin or lactenocin with an enzyme or enzymes produced by certain strains of *Streptomyces thermotolerans* or *Streptomyces fungicidicus*. The enzyme(s) can either be present in or separated from the intact enzyme-producing cells. The derivatives thus prepared are recovered by conventional methods for recovering macrolide antibiotics.

DETAILED DESCRIPTION OF THE INVENTION

This invention relates to new derivatives of macrolide antibiotics and to methods for their production. In particular, it relates to new acylated derivatives of macrocin and lactenocin and to processes for their preparation by bioconversion of macrocin and lactenocin. The new derivatives of this invention are compounds which have formula 1:

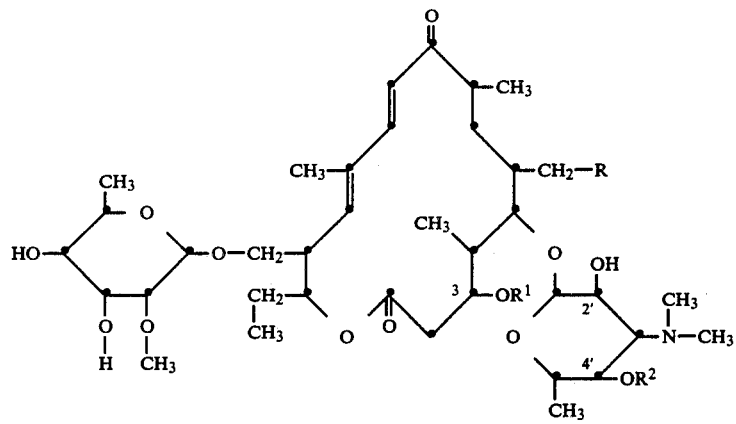

wherein R is formyl or hydroxymethyl; $R^1$ is hydrogen, acetyl or propionyl; $R^2$ is hydrogen or

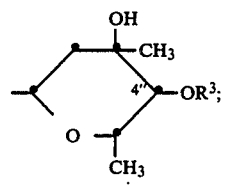

and $R^3$ is hydrogen, acetyl, propionyl, n-butyryl or isovaleryl; provided that one of $R^1$ or $R^3$ must be other than hydrogen; and the acid addition salts of these compounds. Although stereochemical assignments are not indicated in formula 1, the stereochemistry is like that of macrocin.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

Macrocin and lactenocin are antibiotics described by Robert L. Hamill and William M. Stark in U.S. Pat. No. 3,326,759. The structures of macrocin and lactenocin are shown in formulas 2 and 3:

resulted in four derivatives acylated on the 3-hydroxyl group [J. Antibiotics 33 (9), 1083–5 (1980)].

Notwithstanding the biochemical acylation reactions known in the art and the Okamoto teaching that other 16-membered macrolides could be modified in a similar manner, when a new potentially acylatable substrate is presented for biochemical acylation, it is impossible to predict whether acylation will occur because enzymes often have rigid substrate requirements and may not accept a new compound as a substrate. In addition, when different potentially acylatable sites are presented, even if acylation occurs, the position of acylation may be altered from that of other substrates.

Although they are related to tylosin, macrocin and lactenocin contain an additional hydroxyl group (at the 3'''-position), thus presenting an additional potentially acylatable site and possibly different chemical interactions with the enzyme. Thus, it was uncertain that the *Streptomyces thermotolerans* strain which was used to

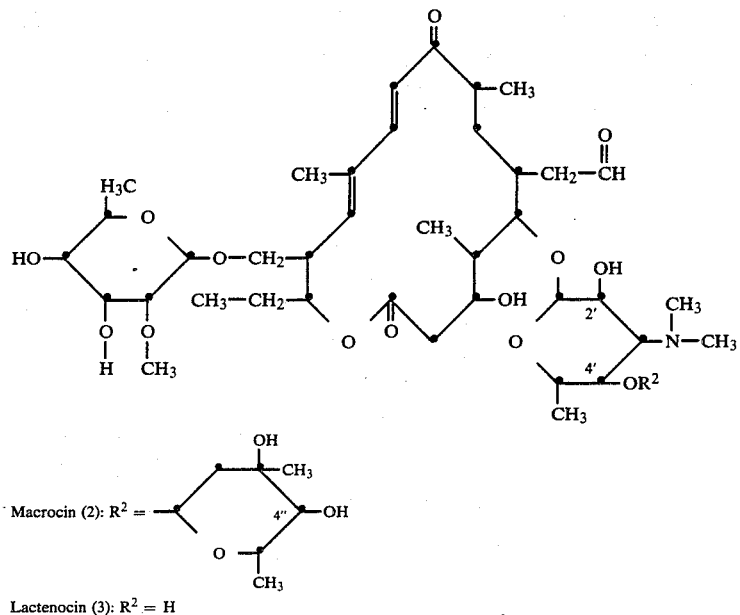

Macrocin (2): $R^2 =$ [structure shown]

Lactenocin (3): $R^2 = H$

Acylation of suitable antibiotics is one method for the production of new derivatives. Ordinarily, chemical processes are used for such acylations. When the antibiotic has multiple acylation sites, however, it is generally necessary to carry out the acylation in several steps, e.g., selectively protecting functional groups in order to obtain a specific product. In contrast, biochemical acylations are generally more selective.

In U.S. Pat. No. 4,092,473, issued May 30, 1978, Okamoto et al. reported biochemical acylation of tylosin at the 3- and 4"-positions using Streptomyces cultures such as *S. thermotolerans* ATCC 11416, *S. fungicidicus* subsp. *espinomyceticus* ATCC 21574, *S. hydroscopicus* ATCC 21582 and *S. mycarofaciens* ATCC 21454.

Macrolide antibiotic N-1, which is 3-O-acetyl-4"-O-isovaleryl-23-demycinosyltylosin, was prepared when 5-O-mycaminosyltylonolide and mycarose were added to a culture of *S. thermotolerans* ATCC 11416 [Japanese unexamined Pat. No. 5043-013 of Sanraku Ocean (Derwent No. 66634C/34)].

U. Graefe et al. reported bioconversion of a platenolide macrolide with a strain of *S. hygroscopicus* which acylate tylosin at the 3- and 4"-positions could also acylate macrocin selectively at these positions and could acylate lactenocin selectively at the 3-position. Since the antibiotic activity of macrocin and lactenocin is less than that of tylosin and desmycosin, respectively, it was especially surprising that the acylated macrocin and lactenocin derivatives have such superior activity against tylosinresistant Mycoplasma strains.

The compounds of the present invention are prepared by contacting macrocin or lactenocin with an acyl donor in the presence of an acylating enzyme system or systems in the form of cells or enzyme preparations. The following organisms possess the appropriate acylating enzyme system for preparing the compounds of this invention: *Streptomyces thermotolerans* strains ATCC 11416 and NRRL 15270 and *Streptomyces fungicidicus* subsp. *espinomyceticus* ATCC 21574.

The *Streptomyces thermotolerans* strain which is preferred for the preparation of the compounds of this invention is the subject of the copending application of Barbara B. Shreve and Jan R. Turner entitled IMPROVED BIOCONVERTING MICROORGANISM, Ser. No. 471,628, filed Mar. 3, 1983. This strain has been deposited and made part of the stock culture collection of the Northern Regional Research Center, Agricultural Research, North Central Region, 1815 North University Street, Peoria, Ill., 61604, from which it is available to the public under the accession number NRRL 15270.

The compounds of formula 1 wherein R is formyl are the preferred compounds of this invention. These compounds are prepared initially in the bioconversion reaction. The compounds of formula 1 wherein R is hydroxymethyl, which are called the "C-20-dihydro" compounds, are prepared by reduction, either chemical or biochemical, of the formula 1 compounds wherein R is formyl.

The compounds of formula 1 wherein $R^2$ is

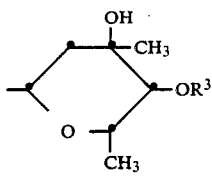

are the macrocin derivatives. These compounds, which are a preferred group of this invention, are prepared when macrocin is used as the substrate in the bioconversion.

The compounds of formula 1 wherein $R^2$ is hydrogen are the lactenocin derivatives. The lactenocin derivatives can be prepared either by using lactenocin in the bioconverting reaction or by acid hydrolysis of the mycarose group from a corresponding macrocin derivative. Procedures for this type of acid hydrolysis are well known in this art.

When carrying out the process of this invention, the organism which produces the converting enzyme(s) is cultivated using procedures generally used for cultivating strains of the genus Streptomyces, but adapting the conditions to get the full acylation potency of the converting enzymes. The culture medium preferably contains carbon sources such as glucose, maltose, sucrose, starch or malt-syrup, alcohols such as ethanol and glycerin, oils, fats and waxes of plant or animal origin, organic acids such as acetic acid and citric acid and salts of these acids. Other assimilable components which serve as such carbon sources, however, can be used. These sources can be used singly or in combinations of two or more in a concentration of 0.5-10 g/dl generally and preferably of 2-6 g/dl, depending upon the sources used. Nitrogen sources include protein-rich organic compounds of animal, plant or microbial origin such as casein, peptone, floured products prepared from soybean, corn, cotton seed and preparations from yeast and bacteria, various conventional inorganic compounds such as ammonium salts, or other nitrogen-rich compounds which can be assimilated by the organism. The nitrogen sources also can be used singly or in combinations in the medium in a concentration of 0.1-10 g/dl. With organic nitrogen sources the preferred concentration is 1-6 g/dl; with inorganic sources, the concentration is lower. The medium also should contain inorganic salts such as phosphates, magnesium salts, mineral salts and growth-promoting materials such as yeast extract, meat extract and vitamins or vitamin-rich materials in concentrations of 0.01-0.5 g/dl, depending on the organism and on the rest of the medium composition.

Cultivation of the organism is carried out aerobically by means of aeration and agitation. The pH of the medium is maintained in the range of from about 4.5 to about 9.0, preferably from 6 to 8. Cultivation temperature is maintained at about 20°–40° C., with 30°–40° C. being a preferred temperature range for *Streptomyces thermotolerans*.

The acylating enzymes are produced early in the growing phase and are maintained after growth has ceased. Acylation of the 3-hydroxyl group is most facile with cells in the early growth phase, and acylation of the 4"-hydroxyl group is most facile with cells from the late growth phase to the stationary phase.

Acylation can be performed with growing cells or with cells at rest either in the cultured medium or after separation from the medium, or with various forms of enzymatic preparations, e.g., dried cells or cell homogenates or the supernatants obtained from cell homogenates. An immobilized enzymatic preparation such as that fixed in an acrylamide polymer, or the immobilized microorganism itself, can also be used.

It appears that, as is the case with tylosin, two enzyme systems are independently included in the acylations. The enzymes have been designated "macrolide 3-acyl transferase" and "macrolide 4"-acyl transferase", since they transfer acyl groups to the 3- and 4"-hydroxyl groups, respectively. These enzyme systems have preferences for particular acyl groups. Macrolide 3-acyl transferase preferably transfers acetyl and propionyl groups, in that order, while macrolide 4"-acyl transferase transfers isovaleryl, n-butyryl and propionyl groups in that order.

Coenzyme A (CoA) is a universal carrier of acyl groups, and acyl CoAs serve as direct donors of the acyl group to be incorporated. The precursor compounds for the respective acyl CoAs are produced in the cell through cell metabolism. Acyl CoAs preferably used include acetyl CoA, propionyl CoA, n-butyryl CoA and isovaleryl CoA: their precursor compounds include organic acids such as acetic acid, propionic acid, n-butyric acid and isovaleric acid, and their salts (e.g., potassium, sodium and ammonium salts, etc.), esters (e.g., methyl and ethyl esters, etc.) and amides. Also included are amino acids such as α-aminobutyric acid, norvaline, L-leucine, and keto acids such as α-ketobutyric acid and α-ketovaleric acid.

In general, acyl CoAs are added to the reaction medium when the reaction is conducted with an enzymatic system with poor ability to generate the acyl CoA from CoA and an acyl precursor. Acyl precursor compounds can be used alone when the system for generating the acyl CoA (e.g., cell growing conditions and the like) is operative. The amount of acyl donor added to the reaction medium usually is approximately equivalent to the antibiotic substrate when the donor is an acyl CoA. When a precursor compound is used, a higher mole ratio (e.g., 3–10 mole ratio) of compound is required.

Living cells can produce acetyl CoA from carbon sources through various metabolic cycles; hence, if a sufficient quantity of carbon source is present in the reaction with living cells, acetylation usually proceeds by the use of endogenously-formed acetyl CoA. In such a reaction system propionyl CoA and other CoAs are produced in far smaller amounts than acetyl CoA, and only a small amount of such acylated products from the former are noted in the reacted mixture.

When an acyl CoA is used in the reaction, CoA can be recovered from the reaction medium by conventional methods for CoA isolation, and the recovered CoA can be reused for the synthesis of acyl CoA.

Macrocin or lactenocin is added to the reaction mixture in forms such as an aqueous solution, a weakly acidic aqueous solution, or a solution in a solvent which exerts little adverse effect on the reaction, e.g., methanol and ethanol. Mixtures of such solvents, e.g. methanol and water, may also be used. The substrate may also be added as a suspension, slurry or fine powder. The concentration of macrocin or lactenocin in the reaction mixture is usually about 0.1–50 g/liter and preferably is 0.5–30 g/liter.

Conditions for the acylating reactions are similar to those used to cultivate the organism producing the enzymes used, but which also favor the enzymatic reactions. Reaction temperatures range from about 25°–43° C., preferably about 28°–40° C. The pH is maintained in the range of 5.0–8.5, preferably at 5.5–8.0 for acylation of the 3-position and 6.5–8.5 for acylation of the 4"-position. An appropriate buffer solution may be used to maintain the pH in reactions in which cells are not growing. Buffer solutions conventionally used for enzymatic reactions, such as phosphate and citrate buffer solutions, etc., may be used. Acetate buffers or buffers containing acetyl groups should be used for acetylation reactions. The reaction period is usually 30 minutes to 10 hours.

The formula 1 compounds of this invention form acid addition salts. These acid addition salts are also useful as antibiotics and are a part of this invention. In another aspect, such salts are useful as intermediates, for example, for separating and purifying the ester derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention.

The derivatives of this invention inhibit the growth of pathogenic bacteria, especially gram-positive bacteria, and Mycoplasma species. For example, Tables I and II summarize the minimal inhibitory concentrations (MIC's) at which illustrative compounds inhibit certain bacteria. The MIC's in Table I were determined by standard agar-dilution assays. The MIC's in Table II were obtained using a conventional broth-dilution microtiter test.

TABLE I

Antibiotic Activity of Formula 1 Compounds

| Test Organism | MIC Values of Test Compounds[e] | | | |
|---|---|---|---|---|
| | 3-Acetyl-macrocin | 3-Acetyl-4"-(n-Butyryl)-macrocin | 3-Acetyl-4"-Isovaleryl-macrocin | 3-Acetyl-lactenocin |
| *Staphylococcus aureus* X1.1 | 0.5 | 1 | 0.5 | 1 |
| *Staphylococcus aureus* V41[a] | 1 | 1 | 1 | 2 |
| *Staphylococcus aureus* X400[b] | 2 | 2 | 2 | 4 |
| *Staphylococcus aureus* S13E | 1 | 2 | 1 | 2 |
| *Staphylococcus epidermidis* EPI1 | 0.5 | 1 | 0.5 | 1 |
| *Staphylococcus epidermidis* EPI2 | 2 | 2 | 2 | 4 |
| *Streptococcus pyogenes* C203 | 0.25 | 0.5 | 0.25 | 0.25 |
| *Streptococcus pneumoniae* Park I | 0.5 | 0.25 | 0.5 | 0.5 |
| *Streptococcus pneumoniae* Group D X66 | 2 | 2 | 2 | 8 |
| *Streptococcus pneumoniae* Group D 9960 | 2 | 2 | 2 | 8 |
| *Haemophilus influenzae* C.L.[c] | 32 | 32 | 32 | 16 |
| *Haemophilus influenzae* 76[d] | 16 | 32 | 16 | 8 |
| *Eschericia coli* TEM | 64 | >128 | 128 | 64 |
| *Klebsiella pneumoniae* X26 | 64 | 64 | 64 | 32 |

[a]Penicillin-resistant strain
[b]Methicillin-resistant-strain
[c]Ampicillin-sensitive strain
[d]Ampicillin-resistant strain
[e]mcg/ml

TABLE II

Antibiotic Activity of Formula 1 Compounds

| Test Organism | MIC Values of Test Compounds[f] | | | |
|---|---|---|---|---|
| | 3-Acetyl-macrocin | 3-Acetyl-4"-(n-Butyryl)-macrocin | 3-Acetyl-4"-Isovaleryl-macrocin | 3-Acetyl-lactenocin |
| *Staphylococcus aureus* | 1.56 | 3.12 | 1.56 | 3.12 |
| Streptococcus sp. 80 | 1.56 | 0.39 | 0.39 | 1.56 |
| *Pasteurella multocida* 17E[a] | 50 | 50 | 50 | 12.5 |
| *Pasteurella multocida* 60A[b] | >50 | 50 | >50 | 25 |
| *Mycoplasma gallisepticum* 38502[c] | 0.78 | 0.195 | ≦0.048 | 0.78 |
| *Mycoplasma gallisepticum* 34159[d] | 50 | 6.25 | 3.12 | >50 |
| *Mycoplasma gallisepticum* 41313[d] | 50 | 3.12 | 3.12 | 50 |
| *Mycoplasma synoviae* 46995 | 0.39 | ≦0.048 | ≦0.048 | 0.39 |
| *Mycoplasma hyorhinis* S-41313 | 6.25 | 0.39 | 0.39 | 25 |

TABLE II-continued

| | Antibiotic Activity of Formula 1 Compounds | | | |
|---|---|---|---|---|
| | MIC Values of Test Compounds[f] | | | |
| Test Organism | 3-Acetyl-macrocin | 3-Acetyl-4''-(n-Butyryl)-macrocin | 3-Acetyl-4''-Isovaleryl-macrocin | 3-Acetyl-lactenocin |
| *Mycoplasma hyopneumonia* S-5972 | NT[e] | 0.048 | 0.048 | NT |

[a]Bovine isolate
[b]Avian isolate
[c]Tylosin-susceptible strain
[d]Tylosin-resistant strain
[e]Not tested
[f]mcg/ml The compounds of this invention have exhibited in vivo activity against experimental infections caused by *Mycoplasma gallisepticum*. In these tests infections were induced in chicks by injecting 0.2 ml of a broth culture of *M. gallisepticum* into the abdominal air sac of one- to three-day-old chicks. The compounds were administered by gavage at a dose equivalent to 0.5 g/gal two times on the day of infection, two times on the day following infection and one time on the third day. Twenty-one days after infection the chicks were weighed, a blood sample was taken, and the chicks were sacrificed. The presence or absence of air-sac lesions was recorded. The results of these tests are summarized in Table III.

TABLE III

| Antimycoplasmal Activity of Macrocin Derivatives in Chicks | | | | |
|---|---|---|---|---|
| | | | *Mycoplasma gallisepticum* | |
| Test Compound | Dosage Level | Mortality | Number with Air-Sac Lesions Number Treated | Number with Antibodies[a]/ Number Tested |
| 3-Acetyl-4''-(n-butyryl)-macrocin | 0.5 g/gal × 5 | 1/7 | 7/10 | 7/9 |
| 3-Acetyl-4''-isovaleryl-macrocin | 0.5 g/gal × 5 | 0/10 | 1/10 | 10/10 |
| Infected Control | 0 | 2/7 | 10/10 | 10/10 |
| Uninfected Control | 0 | 0/10 | 0/10 | 0/10 |

[a]Antibodies to *M. gallisepticum*

The use of the compounds of this invention for controlling mycoplasmal infections is disclosed in the copending application of Earl E. Ose and Jan R. Turner entitled METHOD OF CONTROLLING MYCOPLASMA INFECTIONS, Ser. No. 471,630, filed Mar. 3, 1983, now abandoned. When used for this purpose, an effective amount of a compound of formula 1 is administered parenterally or orally to an infected or susceptible warm-blooded animal. The compounds can also be administered by insufflation, i.e. by blowing the compound, in the form of a medicated dust, into an enclosed space or room wherein the animals or poultry are held. The animals or poultry breathe the medicated dust present in the air; the medicated dust is also taken into the body through the eyes (a process called intraocular injection).

The dose which is effective to control the infection will vary with the severity of the infection and the age, weight, and condition of the animal. The total does required for protection parenterally will generally, however, be in the range of from about 1 to about 100 mg/kg and preferably will be in the range of from about 1 to about 50 mg/kg. The dose required for oral administration will generally be in the range of from 1 to about 300 mg/kg and preferably will be in the range of from about 1 to about 100 mg/kg. Suitable dosage regimens can be constructed.

Often the most practical way to administer the compounds is by formulation into the feed supply or drinking water. A variety of feeds, including the common dry feeds, liquid feeds, and pelleted feeds, may be used.

In their application Ose and Turner also disclose compositions useful for the control of Mycoplasma infections. These compositions comprise a compound of formula 1 together with a suitable vehicle. Compositions may be formulated for parenteral or oral administration by methods recognized in the pharmaceutical art.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing a compound of formula 1.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided:

EXAMPLE 1

Bioconversion of Macrocin to 3-O-Acetylmacrocin, 3-O-Acetyl-4''-O-(n-Butyryl)macrocin and 3-O-Acetyl-4''-O-Isovalerylmacrocin by a Mutant of Streptomyces thermotolerans A. Inoculum Preparation Suitable vegetative inoculum may be obtained by inoculating sterilized medium with lyophilized spore suspensions or spore suspensions obtained by scraping spores from a well sporulated slant of Streptomyces thermotolerans NRRL 15270; best results, however, have been obtained using cultures inoculated from a standardized vegetative inoculum that has been preserved in liquid nitrogen. Liquid-nitrogen-stock inoculum is prepared in the following manner:

A lyophile pellet of S. thermotolerans NRRL 15270 is suspended in sterile water (2 ml). The resulting spore suspension is inoculated into 50 ml of sterile medium in a 250-ml wide-mouth Erlenmeyer flask at a rate of 0.4% volume/volume (v/v). The medium has the following composition:

| Vegetative Medium Composition (CSI) | |
|---|---|
| Ingredient | Amount |
| Glucose | 25 g |
| Soybean grits | 15 g |
| Blackstrap molasses | 3 g |
| Enzyme-hydrolyzed casein[a] | 1 g |
| CaCO$_3$ | 2.5 g |
| Czapek's Mineral Stock[b] | 2 ml |
| Deionized H$_2$O to a total of one liter | |
| pH adjusted to 7.2 prior to sterilization; autoclave 45 minutes | |

[a]Amber EHC (Amber Laboratories, Juneau, WI)
[b]Czapek's Mineral Stock
KCl 100 g
MgSO$_4$.7H$_2$O 100 g
Deionized Water 900 ml
FeSO$_4$.7H$_2$O (2 g) was dissolved in 100 ml distilled water containing 2 ml of concentrated HCl. This solution was added to the above KCl/MgSO$_4$.7H$_2$O solution to complete

| Vegetative Medium Composition (CSI) |
|---|
| preparation of the Czapek's Minerals. |

Flasks containing inoculated media are maintained at 37° C. on a rotary shaker agitating in a 2-inch-diameter arc at 260 RPM for 24 hours. The vegetative culture is then harvested, diluted 1:1 (volume:volume) with a sterile suspending agent of glycerol:lactose:water (2:1:7) and dispensed into sterile tubes (2 ml/tube). The diluted inoculum is then stored over liquid nitrogen in appropriate storage containers and used as a working-stock inoculum for the cultivation of shake-flask conversion cultures and fermenter seed inoculum.

B. General Shake-flask Conversion Procedure

Shake-flask conversions are generally conducted with a culture-volume to flask-volume ratio of 1/5. Sterilized CSI medium is inoculated with liquid-nitrogen-preserved stock inoculum at a rate of 0.4% v/v and incubated at 37° C. on a rotary shaker with a 2-inch-diameter arc at 260 RPM for 22-24 hours. A concentrated methanolic solution containing macrocin and a sterilized, neutralized solution containing DL-norvaline and L-leucine are then added to the converting culture at respective final concentrations of 0.5 mg macrocin/ml and 1.0 mg of each amino acid/ml. The culture is incubated an additional 24 hours as described supra and then is harvested. Conversion-products are recovered by adjusting the pH of the whole culture to about pH 8.5-9.0 and repeatedly extracting with equal volumes of ethyl acetate. Extracts are combined and concentrated under vacuum to dryness. The various conversion products are recovered in purified form via reversed-phase (RP) high performance liquid chromatography (HPLC).

In general, shake-flask conversions result in complete conversion of substrate to the corresponding 3-O-acetyl derivative in 8-10 hours, followed by subsequent conversion of the 3-O-acetyl intermediate to the 3-O-acetyl-4''-O-(n-butyryl) and/or 3-O-acetyl-4''-O-isovaleryl derivatives. Extension of the conversion time beyond 24-28-hours results in the partial conversion of products to the C-20 dihydro-derivative.

C. General Procedure for Conversion in Stirred Fermenters

Seed inoculm for stirred fermenters (tanks) is prepared by inoculating 200 ml of sterile CSI medium in a one-liter wide-mouth Erlenmyer flask with liquid-nitrogen-stock inoculum at a rate of 0.4% v/v. The seed culture is then incubated at 37° C. on a rotary shaker with a 2-inch diameter arc at 260 RPM for 22 hours. The resulting vegetative culture is used to inoculated a stirred fermenter containing 25 liters of sterile medium (0.8% inoculm, v/v) which has the following composition:

| Tank Fermentation Medium | |
|---|---|
| Ingredient | Amount |
| Antifoam agent[a] | 0.2 g |
| Glucose | 25 g |
| Soybean grits | 15 g |
| Blackstrap molasses | 3 g |
| Casein | 1 g |
| CaCO$_3$ | 5 g |
| Czapek's Mineral Stock | 2 ml |

| Tank Fermentation Medium | |
|---|---|
| Ingredient | Amount |
| Deionized water q.s. to | 1 liter |

[a] Dow Corning (Chicago, IL)
Sterilize for 45 minutes at about 126° C. and 20–23 psi Fermentation temperature is maintained at 37° C. Two 6-blade 6-inch-diameter impellers mounted on the fermenter impeller shaft are rotated at 300 RPM to provide agitation. The culture is aerated by sparging sterile air into the fermenter below the bottom impeller at a rate of 0.5 v/v/m. Sterilized, neutralized solutions (2 L.) containing DL-norvaline (25 g), L-leucine (25 g) and 50–100 ml of a solution of macrocin (12.5 g) in methanol are added to the culture after 22–24 hours of growth. Fermentation is continued for an additional 22–24 hours, although in most cases conversion is complete in 12–16 hours.

Macrocin is rapidly converted to 3-O-acetyl macrocin, usually within three hours after substrate addition. Conversion of 3-O-acetyl macrocin to the 3-O-acetyl-4″-O-(n-butyryl)macrocin and 3-O-acetyl-4″-O-isovalerylmacrocin derivatives occurs at a somewhat slower rate. Maximum 4″-ester formation usually occurs about 7–16 hours after substrate addition. When the converting culture is harvested about 7–8 hours after substrate addition, conversion to the 3,4″-diester is approximately 85–95% complete and formation of the C-20-dihydro products is minimized.

When preparing 3-O-acetyl-4″-O-isovalerylmacrocin, it is preferable to add L-leucine (50 g per 25 liters of culture) to the medium.

When C-20-dihydro compounds are desired, the fermentation is carried out for a longer period of time, preferably from about 22 to about 30 hours.

D. Assay Procedure

This assay method is useful for monitoring the bioconversion process and for isolating the individual bioconversion products: A sample (4 ml) of whole broth containing bioconversion product(s) is adjusted to pH 9.0 with NaOH and extracted once with ethyl acetate (2 ml). The resulting suspension is centrifuged, and the ethyl acetate portion is analyzed by reversed-phase HPLC, using Waters μ-Bondapak C-18 or Merck Li-Chrosorb RP-18 as the adsorbent. 3-O-Acetylmacrocin is assayed using the solvent system $H_2O$/MeOH/NH$_4$COOH (40/60/0.2), while the 3,4″-diesters are assayed with the system $H_2O$/MeOH/NH$_4$COOH (25/75/0.2). Macrocin and the ester derivatives are detected by ultraviolet (UV) absorption at 280 nm.

E. Isolation of Conversion Products

The pH of the fermentation broth is adjusted to about 8.5 with sodium hydroxide. Ethyl acetate (two volumes) is added with vigorous stirring. The resulting emulsion is passed through a Sepa centrifuge to sediment cellular debris and break the emulsion. Cell debris and the aqueous phase are discarded. The organic layer is concentrated under vacuum to an oily residue which is repeatedly triturated with hexane until an oil-free dry crude preparation is obtained. The yield of crude preparation is in the range of 3–9 g.

The crude dried preparation is subjected to repeated purification via reverse-phase HPLC until the appropriate derivative is obtained in pure form.

Initially, 3-O-acetylmacrocin is separated from the diesters by preparative HPLC (Waters Prep/500-reversed-phase) of crude dried extract (in amounts of about 3–7 g), using the solvent system $H_2O$/CH$_3$CN/diethylamine (65/35/0.1). Diesters are partially separated from each other using the system $H_2O$/CH$_3$CN/pyridine/HOAc (65/35/1.5/0.5). Appropriate fractions, as determined by UV at 280 nm and analytical HPLC, are combined, concentrated to the aqueous phase and lyophilized to yield dry preparations.

The mono- and diesters are further purified by HPLC with either 38″×½″ or 25.5″×1″ LP-1/C$_{18}$ columns with the appropriate solvent system:

| Compound | Solvent System | Ratio |
|---|---|---|
| 3-O—acetylmacrocin | $H_2O$/CH$_3$CN/NH$_4$HCO$_3$ | (70/30/0.001) |
| 3-O—acetyl-4″-O—(n-butyryl)macrocin and 3-O—acetyl-4″-O—isovaleryl-macrocin | $H_2O$/CH$_3$CN/pyridine/HOAc | (70/30/1.5/0.5) |

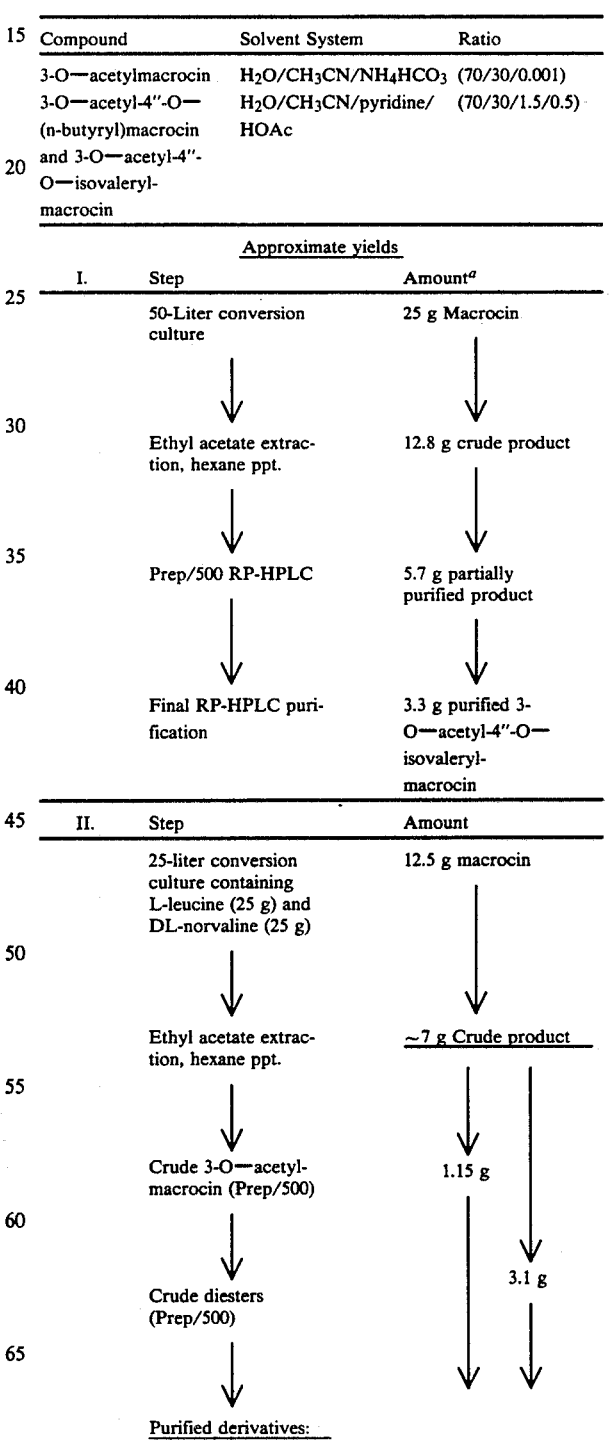

Approximate yields

I.
| Step | Amount[a] |
|---|---|
| 50-Liter conversion culture | 25 g Macrocin |
| Ethyl acetate extraction, hexane ppt. | 12.8 g crude product |
| Prep/500 RP-HPLC | 5.7 g partially purified product |
| Final RP-HPLC purification | 3.3 g purified 3-O—acetyl-4″-O—isovaleryl-macrocin |

II.
| Step | Amount |
|---|---|
| 25-liter conversion culture containing L-leucine (25 g) and DL-norvaline (25 g) | 12.5 g macrocin |
| Ethyl acetate extraction, hexane ppt. | ~7 g Crude product |
| Crude 3-O—acetyl-macrocin (Prep/500) | 1.15 g |
| Crude diesters (Prep/500) | 3.1 g |
| Purified derivatives: | |

-continued

| | |
|---|---|
| 3-O—acetylmacrocin | 98.5 g |
| 3-O—acetyl-4″-O—(n-butyryl)macrocin | 461 mg |
| 3-O—acetyl-4″-O—isovalerylmacroin | 548 mg |

Field-desorption mass spectrometry (FDMS) gave the following parent ions:

| Compound | M + 1 |
|---|---|
| 3-O—Acetylmacrocin | 944 |
| 3-O—Acetyl-4″-O—(n-butyryl)macrocin | 1014 |
| 3-O—Acetyl-4″-O—isovalerylmacrocin | 1028 |

EXAMPLE 2

Preparation of 3-O-Acetyllactenocin from 3-O-Acetylmacrocin

3-O-Acetylmacrocin (350 mg) was added to 1N sulfuric acid (43 ml). The resulting solution was stirred for about one hour at room temperature and then neutralized with concentrated aqueous $NaHCO_3$ solution (to about pH 7.5). The pH of this solution was adjusted to 8.5 by the addition of NaOH; the solution was then extracted five times with ethyl acetate (equal volumes). The ethyl acetate extracts were combined, dried over anhydrous $Na_2SO_4$, and evaporated to yield crude 3-O-acetyllactenocin (302.5 mg).

This material was purified by HPLC using a 38-inch×½-inch LP-1/$C_{18}$ silica-gel column and eluting with a $H_2O/CH_3CN$/pyridine/HOAc (78.4/19.6/1.5/0.5) solvent system at a flow rate of about 5 ml/minute. Appropriate fractions were identified by analytical HPLC on a HIBAR II column (LiChrosorb RP-18, 250×4.6 mm, Merck), using a solvent system of $H_2O/CH_3CN$ (3:1) containing 2% pyridinium acetate, at a flow rate of 2 ml/min. and detecting with UV at 280 nm. The desired fractions were combined and evaporated to give 165.5 mg of 3-O-acetyllactenocin; FDMS mass ion (M+1)=800.

Nuclear magnetic resonance (NMR) spectra of the compounds of Examples 1 and 2 are summarized in Table IV ($\delta$, $CDCl_3$).

TABLE IV

| Carbon Location | NMR Resonances of Formula 1 Compounds | | | |
|---|---|---|---|---|
| | 3-Acetyl-macrocin | 3-Acetyl-4″-(n-Butyryl)-macrocin | 3-Acetyl-4″-Isovaleryl-macrocin | 3-Acetyl-lactenocin |
| 2 | ~2.5/~1.9 | ~2.5/~1.9 | ~2.5/~1.9 | NA/NA |
| 3 | 5.16 | 5.16 | 5.16 | 5.17 |
| 4 | ~1.6 | ~1.6 | ~1.6 | ~1.6 |
| 5 | ~3.5 | ~3.5 | ~3.5 | ~3.5 |
| 6 | 2.16 | ~2.1 | ~2.1 | ~2.1 |
| 7 | 1.44/NA$^a$ | 1.44/NA | 1.44/NA | NA/NA |
| 8 | ~2.7 | ~2.7 | ~2.7 | NA |
| 10 | 6.24 | 6.28 | 6.26 | 6.26 |
| 11 | 7.38 | 7.41 | 7.40 | 7.40 |
| 13 | 5.95 | 5.94 | 5.95 | 5.95 |
| 14 | 3.00 | 3.00 | 3.00 | 3.00 |
| 15 | 4.80 | 4.80 | 4.81 | 4.80 |
| 16 | ~1.6/~1.9 | ~1.6/~1.9 | ~1.6/~1.9 | NA |
| 17 | 0.88 | 0.92 | 0.92 | 0.92 |
| 18 | 1.02 | 1.06 | 1.04 | 1.07 |
| 19 | 2.64/NA | ~2.64/NA | ~2.64/NA | NA |
| 20 | 9.61 | 9.64 | 9.63 | 9.63 |
| 21 | 1.24 | 1.24 | 1.24 | 1.24 |
| 22 | 1.78 | 1.82 | 1.80 | 1.82 |
| 23 | 3.99/~3.5 | 3.98/~3.5 | 3.99/~3.5 | 3.99/~3.5 |
| 1′ | 4.16 | 4.17 | 4.18 | 4.18 |
| 2′ | ~3.5 | ~3.5 | ~3.5 | ~3.5 |
| 3′ | ~2.5 | ~2.5 | ~2.5 | ~2.5 |
| 4′ | 3.26 | 3.28 | 3.28 | 3.04 |
| 5′ | 3.26 | 3.28 | 3.28 | 3.25 |
| 6′ | 1.24 | 1.24 | 1.24 | ~1.27 |
| $N(CH_3)_2$ | 2.50 | 2.52 | 2.50 | 2.50 |
| 1″ | 5.06 | 5.06 | 5.07 | — |
| 2″ | ~2.1/1.78 | ~2.1/~1.8 | ~2.1/~1.8 | — |
| 4″ | ~3.0 | 4.62 | 4.63 | — |
| 5″ | 4.05 | 4.45 | 4.43 | — |
| 6″ | 1.30 | 1.13 | 1.13 | — |
| 7″ | 1.24 | 1.13 | 1.12 | — |
| 1‴ | 4.52 | 4.52 | 4.53 | 4.53 |
| 2‴ | 3.06 | 2.98 | 3.00 | 2.99 |
| 3‴ | 4.16 | 4.17 | 4.18 | ~4.18 |
| 4‴ | 3.26 | 3.24 | 3.22 | 3.22 |
| 5‴ | 3.64 | 3.63 | 3.64 | 3.64 |
| 6‴ | 1.30 | 1.30 | 1.30 | ~1.27 |
| $OCH_3$ | 3.44 | 3.48 | 3.46 | 3.46 |
| OAc | 2.10 | 2.12 | 2.11 | 2.13 |
| $CH_3\ CH_3$ – $CH$ | — | — | 1.00 ~2.1 | — |
| $CH_2$ | —· | — | 2.29 | — |
| $CH_3$ | — | 0.98 | — | — |
| $CH_2$ | — | ~1.7 | — | — |
| $CH_2$ | — | 2.39 | — | — |

EXAMPLE 3

3-O-Acetyllactenocin can be prepared using the method of Example 1 with lactenocin as the substrate.

EXAMPLE 4

20-Dihydro-3-O-Acetylmacrocin can be prepared by reacting 3-O-acetylmacrocin with sodium borohydride in an aqueous solution of an alcohol such as isopropyl alcohol until reduction of the formyl group at C-20 is complete.

EXAMPLE 5

4″-O-Isovalerylmacrocin can be prepared by the procedure of Example 1, but using a medium containing restricted concentrations of carbon and nitrogen sources and adding macrocin when the carbon sources are almost consumed. The product, which is co-produced with other 3-O-acylated macrocin and 3-O-acyl-4″-O-isovalerylmacrocin products, is separated from the co-produced products by chromatographic methods, e.g. reversed-phase HPLC as in Example 1.

EXAMPLES 6–15

Other compounds of this invention which can be prepared using the procedures of the preceding examples include:
3-O-propionylmacrocin
3-O-propionyllactenocin
3-O-propionyl-4″-(n-butyryl)macrocin
3-O-acetyl-4″-O-acetylmacrocin 3-O-propionyl-4"-O-isovalerylmacrocin
4"-O-(n-butyryl)macrocin
3-O-acetyl-20-dihydromacrocin
3-O-acetyl-20-dihydromacrocin
3-O-acetyl-20-dihydro-4"-isovalerylmacrocin
20-dihydro-3-O-propionyllactenocin

EXAMPLE 16

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

EXAMPLE 17

Chick Ration for Control of Mycoplasma

A balanced, high-energy ration adapted to feed chicks for rapid weight gain is prepared by the following recipe:

| Ingredient | Percent | Lbs/Ton |
|---|---|---|
| Ground yellow corn | 53.46 | 1069.2 |
| Soybean meal, solvent-extracted dehulled, finely ground, 48 percent protein | 31.73 | 634.6 |
| Animal-vegetable fat | 2.83 | 56.6 |
| Dried fish meal | 5.0 | 100 |
| Distillers' solubles from corn | 4.0 | 80 |
| Dicalcium phosphate, feed grade | 1.28 | 25.6 |
| Ground limestone | 0.62 | 12.4 |
| Salt | 0.3 | 6.0 |
| Vitamin premix[1] | 0.5 | 10 |
| Trace mineral premix[2] | 0.1 | 2 |
| 2-Amino-4-hydroxybutyric acid (hydroxy analog of methionine) | 0.17 | 3.4 |
| Formula 1 compound | 0.01 | 0.2 |

[1]Vitamin premix provides 3000 IU of vitamin A, 900 ICU of vitamin D₃, 40 mg of vitamin E, 0.7 mg of vitamin K, 1000 mg of choline, 70 mg of niacin, 4 mg of pantothenic acid, 4 mg of riboflavin, 100 mcg of vitamin B₁₂, 100 mcg of biotin and 125 mg of ethoxyquin per kg of complete feed.
[2]Trace mineral premix provides 75 mg of manganese, 50 mg of zinc, 25 mg of iron and 1 mg off iodine per kg of complete feed.

These substances are mixed in accordance with standard feed-mixing techniques. Chicks fed such a ration, with water ad libitum, are protected against exposure to mycoplasmal infections.

We claim:
1. A compound of the formula

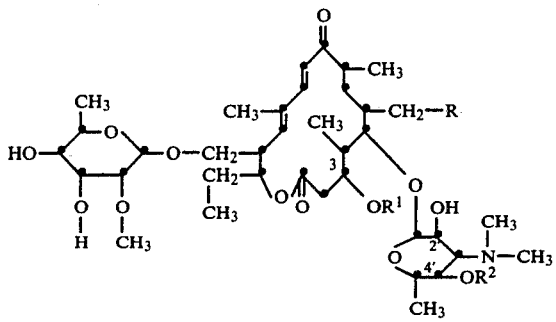

wherein
R is formyl or hydroxymethyl;
$R^1$ is hydrogen, acetyl or propionyl;
$R^2$ is hydrogen or

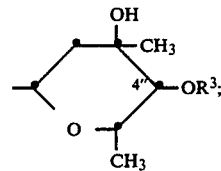

and
$R^3$ is hydrogen, acetyl, propionyl, n-butyryl or isovaleryl; provided that one of $R^1$ or $R^3$ must be other than hydrogen; and the acid addition salts thereof.

2. A compound of claim 1 wherein R is formyl.
3. A compound of claim 2 wherein $R^2$ is

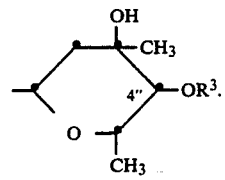

4. A compound of claim 3 wherein $R^1$ is acetyl.
5. The compound of claim 4 wherein $R^3$ is hydrogen.
6. The compound of claim 4 wherein $R^3$ is n-butyryl.
7. The compound of claim 4 wherein $R^3$ is isovaleryl.
8. A compound of claim 2 wherein $R^2$ is hydrogen.
9. A compound of claim 8 wherein $R^1$ is acetyl.
10. A compound of claim 1 wherein R is hydroxymethyl.
11. A compound of claim 10 wherein $R^2$ is

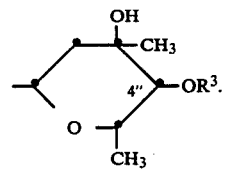

12. A compound of claim 10 wherein $R^2$ is hydrogen.

* * * * *